US006964935B2

(12) United States Patent
Harris et al.

(10) Patent No.: US 6,964,935 B2
(45) Date of Patent: Nov. 15, 2005

(54) MORDENITE ZEOLITE ALKYLATION CATALYSTS

(75) Inventors: Thomas V. Harris, Benicia, CA (US); Curt B. Campbell, Hercules, CA (US); Pierre Tequi, Breaute (FR); Jean-Louis Le Coent, Le Havre (FR)

(73) Assignees: Chevron Oronite Company LLC., San Ramon, CA (US); Chevron Oronite S.A., Gonfreville-L Orcher (FR)

( * ) Notice: Subject to any disclaimer, the term of this patent is extended or adjusted under 35 U.S.C. 154(b) by 0 days.

(21) Appl. No.: 10/800,099

(22) Filed: Mar. 12, 2004

(65) Prior Publication Data

US 2005/0203323 A1    Sep. 15, 2005

(51) Int. Cl.$^7$ .............................................. B01J 29/18
(52) U.S. Cl. ......................................... 502/78; 502/60
(58) Field of Search ..................................... 502/60, 78

(56) References Cited

U.S. PATENT DOCUMENTS

| | | | |
|---|---|---|---|
| 3,094,383 A | 6/1963 | Dzierzanowski et al. | |
| 3,119,660 A | 1/1964 | Howell et al. | |
| 3,288,716 A | 11/1966 | Becraft et al. | |
| 3,641,177 A | 2/1972 | Eberty, Jr. et al. | |
| 3,764,533 A | 10/1973 | Hunt et al. | |
| 3,777,006 A | 12/1973 | Rundell et al. | |
| 3,929,672 A | 12/1975 | Ward | |
| 4,123,390 A | * 10/1978 | Sherman et al. | ............ 426/561 |
| 4,185,040 A | 1/1980 | Ward et al. | |
| 4,259,193 A | 3/1981 | Tirtiaux et al. | |
| 4,764,295 A | 8/1988 | Le Coent | |
| 4,891,448 A | 1/1990 | Garces et al. | |
| 5,004,841 A | 4/1991 | Lee et al. | |
| 5,112,506 A | 5/1992 | Marsh et al. | |
| 5,118,896 A | 6/1992 | Steigelmann et al. | |
| 5,175,135 A | 12/1992 | Lee et al. | |
| 5,191,135 A | 3/1993 | Dwyer et al. | |
| 5,198,595 A | 3/1993 | Lee et al. | |
| 5,243,116 A | 9/1993 | Lee et al. | |
| 5,453,553 A | 9/1995 | Sivasanker et al. | |
| 5,922,922 A | 7/1999 | Harris et al. | |
| 5,939,594 A | 8/1999 | Le Coent | |
| 6,031,144 A | 2/2000 | Campbell et al. | |
| 6,337,310 B1 | 1/2002 | Campbell et al. | |
| 6,525,234 B1 | 2/2003 | Dandekar et al. | |

OTHER PUBLICATIONS

S. Sivasanker, A. Thangaraj, "Distribution of Isomers in the Alkylation of Benzene with Long-Chain Olefins over Solid Acid Catalysts", *Journal of Catalysis*, 138, 386-390 (1992), no month.

* cited by examiner

*Primary Examiner*—Elizabeth D. Wood
(74) *Attorney, Agent, or Firm*—Sarita R. Kelley

(57) ABSTRACT

The present invention is directed to a mordenite zeolite catalyst having a controlled macropore structure. The present invention is also directed to a mordenite zeolite catalyst composite and a process for preparing the catalyst composite. The catalyst composite exhibits reduced deactivation rates during the alkylation process, thereby increasing the life of the catalyst.

23 Claims, 1 Drawing Sheet

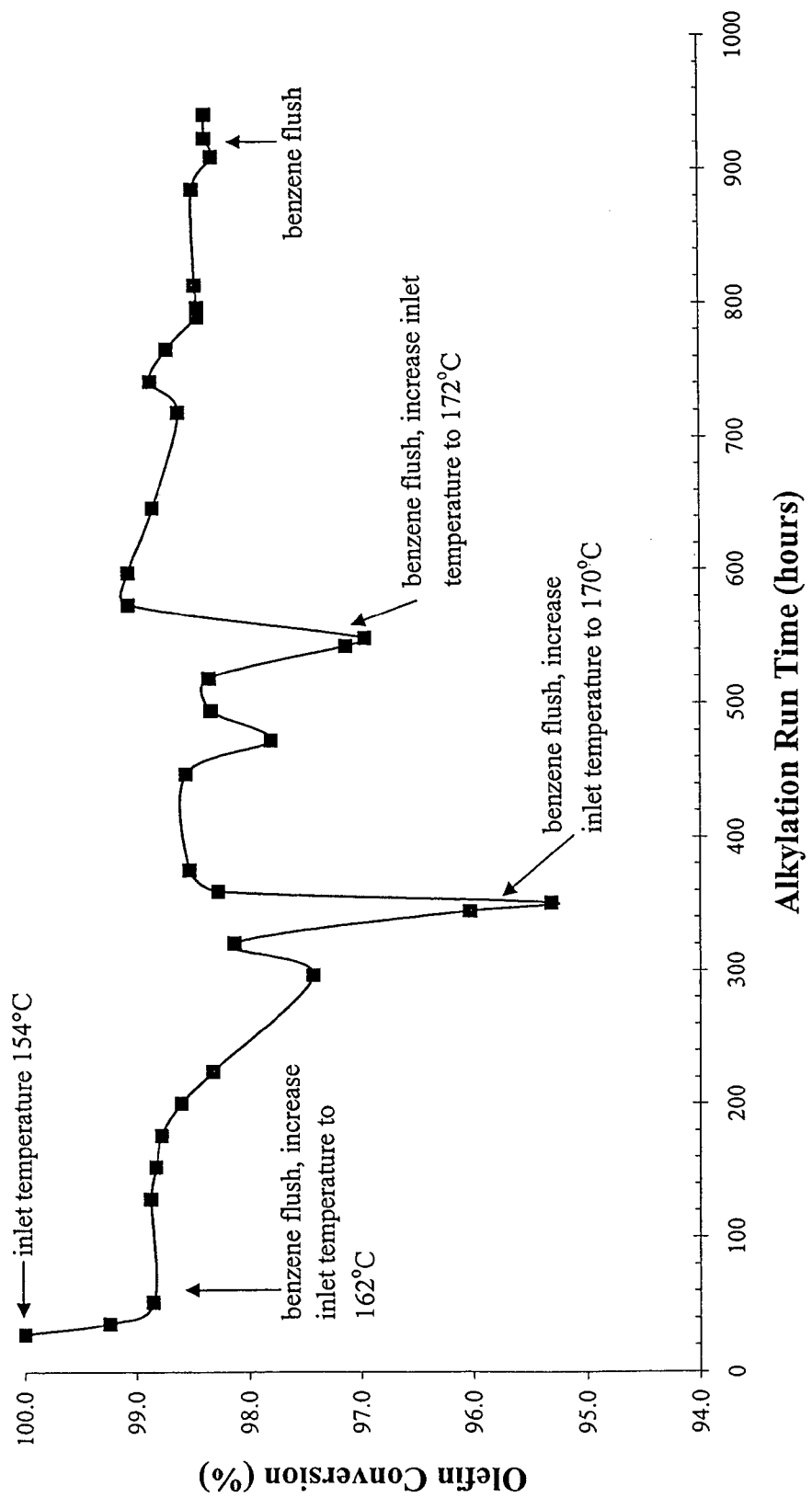

MORDENITE ZEOLITE ALKYLATION CATALYSTS

FIELD OF THE INVENTION

The present invention is directed to a mordenite zeolite catalyst having a controlled macropore structure. The present invention is also directed to catalyst composites comprising mordenite zeolite and a process for preparing the catalyst composites. The present invention is also directed to alkylation of aromatic hydrocarbons using the catalysts and the catalyst composites of this invention. The catalysts and the catalyst composites exhibits reduced deactivation rates during the alkylation process, thereby increasing the life of the catalysts and the catalyst composites as evidenced by the longer alkylation run length times. The catalysts and the catalyst composites of this invention are also capable of being reactivated with a aromatic hydrocarbon flush.

BACKGROUND OF THE INVENTION

It is well known to catalyze the alkylation of aromatics with a variety of Lewis or Bronsted acid catalysts. Typical commercial catalysts include phosphoric acid/kieselguhr, aluminum halides, boron trifluoride, antimony chloride, stannic chloride, zinc chloride, onium poly(hydrogen fluoride), and hydrogen fluoride. Alkylation with lower molecular weight olefins, such as propylene, can be carried out in the liquid or vapor phase. For alkylations with higher olefins, such as $C_{16}$ olefins, the alkylations are done in the liquid phase, usually in the presence of hydrogen fluoride. Alkylation of benzene with higher olefins is especially difficult, and requires hydrogen fluoride treatment. However, hydrogen fluoride is not environmentally attractive.

The use of the above listed acids is extremely corrosive, thus requiring special handling and equipment. Also, the use of these acids might involve environmental problems. Another problem is that the use of these acids can give less than desirable control on the precise chemical composition of the product produced. Thus, it would be preferable to use a safer, simpler catalyst, preferably in solid state. This simpler process would result in less capital investment, which would result in a less expensive product.

Solid crystalline aluminosilicate zeolite catalysts have been known to be effective for the alkylation of aromatics with olefins. Zeolitic materials which are useful as catalysts are usually inorganic crystalline materials that possess uniform pores with diameters in micropore range that is less than 20 angstroms. Zeolites occur naturally and may also be prepared synthetically. Synthetic zeolites include, for example, zeolites A, X, Y, L and mordenite. It is also possible to generate metaloaluminophosphates and metalosilicophosphates. Other materials, such as boron, gallium, iron or germanium, may also be used to replace the aluminum or silicon in the framework structure.

These zeolite catalyst materials are commercially available as fine crystalline powders for further modification to enhance their catalytic properties for particular applications. Processes for the further modification to enhance catalytic properties of the crystalline zeolite catalysts are well known in the art, such as forming the zeolite catalysts into shaped particles, exchanging the cations in the catalyst matrix, etc.

Forming the zeolite powders into shaped particles may be accomplished by forming a gel or paste of the catalyst powder with the addition of a suitable binder material such as a clay, an inorganic compound, or an organic compound and then extruding the gel or paste into the desired form. Zeolite powders may also be formed into particles without the use of a binder. Typical catalyst particles include extrudates whose cross sections are circular or embrace a plurality of arcuate lobes extending outwardly from the central portion of the catalyst particles.

One problem with catalyst particles used in fixed bed reactors is catalyst deactivation. In most hydrocarbon conversion processes, including alkylation, the primary catalyst deactivation is caused by coke formation. This catalyst deactivation is a serious problem in the use of zeolite catalysts for alkylation reactions. This deactivation problem is well known in the art and it is well understood that the deactivation mechanism can involve polymerization of the olefin into large molecular species that cannot diffuse out of the pores containing the active sites in the zeolitic material.

The use of zeolite catalysts for preparation of alkylated aromatic hydrocarbons is typically conducted by the catalytic alkylation of aromatic hydrocarbons with normal alpha olefins or branched-chain olefins, and optionally a promotor.

A number of patents have discussed processes for the preparation of zeolite catalysts and the further shaping and forming of the catalyst particles and extrudates with and without the use of binders. There are also a number of patents disclosing the use of zeolite catalysts for alkylation of aromatic hydrocarbons.

U.S. Pat. No. 3,094,383 discloses the preparation of synthetic zeolite materials which upon hydration yield a sorbent of controlled effective pore diameter and in which the sorbent and its zeolite precursor are provided directly in the form of an aggregate.

U.S. Pat. No. 3,119,660 discloses a process for making massive bodies or shapes of crystalline zeolites. The patent also discloses methods for the identification of the catalyst materials using X-ray powder diffraction patterns in conjunction with chemical analyses.

U.S. Pat. No. 3,288,716 discloses that the high "heavy content" of the alkylated aromatic product can be controlled during the alkylation step and has advantages over distilling the alkylated aromatic product to obtain the desired molecular weight.

U.S. Pat. Nos. 3,641,177 and 3,929,672 disclose the technique to remove sodium or other alkali metal ions from zeolite catalysts. The '177 patent also discloses that such removal of the sodium or other alkali metal ions activates the zeolite catalysts for the alkylation of aromatic hydrocarbons with olefins by liquid phase reaction.

U.S. Pat. Nos. 3,764,533, 4,259,193 and 5,112,506 disclose the "heavy alkylate" content influences neutral sulfonates and overbased sulfonates. In U.S. Pat. No. 5,112,506, the effect of molecular weight distribution or "heavy alkylate" is shown to influence the performance of both Neutral and HOB sulfonates and the di-alkylate content is shown to influence the rust performance of the corresponding sulfonate in U.S. Pat. No. 3,764,533. In U.S. Pat. No. 4,259,193, a mono-alkylate sulfonate is preferred. U.S. Pat. Nos. 3,288,716; 3,764,533; 4,259,193; and 5,112,506 are hereby incorporated by reference for all purposes.

U.S. Pat. No. 3,777,006 discloses the use of nucleating centers for the crystallization of crystalline aluminosilicate zeolites having a size in excess of 200 microns and characterized by high strength and excellent adsorptive properties.

U.S. Pat. No. 4,185,040 discloses the preparation of highly stable and active catalysts for the alkylation of aromatic hydrocarbons with $C_2$–$C_4$ olefins. The catalysts are acidic crystalline aluminosilicate zeolites which exhibit much improved deactivation rates.

U.S. Pat. No. 4,764,295 discloses a process for making non-foaming detergent-dispersant lubricating oil additives. The process further involves carbonation for making the products more basic.

U.S. Pat. No. 4,891,448 discloses a process for alkylation of polycyclic aromatic compounds in the presence of an acidic mordenite zeolite catalyst having a silica to alumina molar ratio of at least 15:1 to produce a mixture of substituted polycyclic aromatic compounds enriched in the para alkylated isomers.

U.S. Pat. No. 5,004,841 discloses a process for alkylation of polycyclic aromatic compounds in the presence of an acidic mordenite zeolite catalyst having a silica to alumina molar ratio of at least 15:1 to produce substituted polycyclic aromatic compounds enriched in the linear alkylated isomers.

U.S. Pat. No. 5,118,896 discloses an aromatic alkylation process comprising the steps of contacting a aromatic hydrocarbon feed with an alkylating agent under liquid phase alkylation conditions in the presence of a silica-containing large macropore, small particle size zeolite catalyst, the catalyst having a pore volume of about 0.25 to 0.50 cc/g in pores having a radius of 450 angstroms and a catalyst particle diameter of not more than $\frac{1}{32}$ of an inch.

U.S. Pat. No. 5,175,135 discloses the use of an acidic mordenite zeolite catalyst for alkylation of aromatic compounds with an alkylating agent having from one carbon atom to eight carbon atoms to produce substituted aromatic compounds enriched in the linear alkylated isomers. The acidic mordenite catalyst is characterized by its silica to alumina molar ratio, its porosity and a Symmetry Index.

U.S. Pat. No. 5,191,135 discloses the process for making long-chain alkyl-substituted aromatic compounds from naphthalenes, the process comprising a zeolite alkylation catalyst in the presence of 0.5 to 3.0 weight percent water. The presence of water increases the selectivity for making mono-alkylated products.

U.S. Pat. No. 5,198,595 discloses a process for alkylation of benzene or substituted benzene in the presence of an acidic mordenite zeolite catalyst having a silica to alumina ratio of at least 160:1 and a Symmetry Index above about 1.0. A process for the preparation of the catalyst is also disclosed.

U.S. Pat. No. 5,243,116 discloses the production of alkylated benzenes by alkylation and/or transalkylation in the presence of an acidic mordenite zeolite catalyst having a silica to alumina molar ration of at least 30:1 and a specific crystalline structure determined by X-ray diffraction.

U.S. Pat. Nos. 5,240,889 and 5,324,877 disclose processes for the preparation of a catalyst composition having alkylation and/or transalkylation activity and wherein the catalyst composition contains greater than 3.5 weight percent water based on the total weight of the catalyst composition and the aromatic alkylation process using said catalyst composition and olefins containing 2 carbon atoms to 25 carbon atoms.

U.S. Pat. No. 5,453,553 discloses a process for the production of linear alkyl benzenes which process comprises co-feeding a mixture of benzene, linear olefins and molecular hydrogen in the presence of a zeolite catalyst containing a transition metal under alkylation condition such that the catalyst is not deactivated.

U.S. Pat. No. 5,922,922 discloses a process for isomerizing a normal alpha olefin in the presence of an acidic catalyst having a one-dimensional pore system, and then use of the isomerized olefin to alkylate aromatic hydrocarbons in the presence of a second acidic catalyst, which can be mordenite zeolite having a silica to alumina ratio of at least 40 to 1.

U.S. Pat. No. 5,939,594 discloses the preparation of a superalkalinized alkylaryl sulfonate of alkaline earth metal. The alkyl group of the alkylaryl sulfonate contains between 14 to 40 carbon atoms and the aryl sulfonate radical of alkaline earth metal is fixed in a molar proportion comprised between 0 and 13% in positions 1 or 2 of the linear alkyl chain.

U.S. Pat. No. 6,031,144 discloses a process for reducing the residual olefin content of an alkylation reaction product by removing at least a portion of the non-alkylated single-ring aromatic hydrocarbon and then reacting the remaining alkylation reaction product in the presence of an acidic catalyst such as a molecular sieve or clay.

U.S. Pat. No. 6,337,310 discloses the preparation of alkylbenzene from preisomerized normal alpha olefins for making low overbased and high overbased sulfonates having a total base number between 3 and 500. The process uses HF as catalyst or a solid acidic alkylation catalyst, such as a zeolite having an average pore size of at least 6 angstroms.

U.S. Pat. No. 6,525,234 discloses a process for alkylating aromatic using a porous crystalline material, e.g., MCM-22 and in situ regenerating the catalyst by use of a polar compound having a dipole moment of at least 0.05 Debyes.

It is known that most solid acid catalysts produce high 2-aryl attachment when alkylating with alpha-olefins. See S. Sivasanker, A. Thangaraj, "Distribution of Isomers in the Alkylation of Benzene with Long-Chain Olefins over Solid Acid Catalysts," *Journal of Catalysis*, 138, 386–390 (1992). This is especially true for mordenite zeolite.

Two general treatises on zeolite are: Handbook of Molecular Sieves by Rosemarie Szostak (Van Nostrand Reinhold, New York 1992) and *Molecular Sieves: Principles of Synthesis and Identification*, $2^{nd}$ Edition, by Rosemarie Szostak (Chapman and Hall, London, UK 1999).

SUMMARY OF THE INVENTION

The present invention is directed to a mordenite zeolite catalyst having a controlled macropore structure. The present invention is also directed to catalyst composites comprising mordenite zeolite and a process for preparing the catalyst composites. The present invention is also directed to processes for preparation of alkylated aromatic hydrocarbons, which processes comprise the alkylation in the presence of the catalysts and catalyst composites of this invention.

The catalysts and the catalyst composites exhibits reduced deactivation rates during the alkylation process, thereby increasing the life of the catalysts and the catalyst composites, as evidenced by the longer alkylation run length times.

In particular, the present invention is directed to catalysts having a macropore structure comprising mordenite zeolite having a silica to alumina molar ratio in the range of about 50:1 to about 105:1 and wherein the peak macropore diameter of the catalyst, measured by ASTM Test No. D 4284-03, is less than or equal to about 900 angstroms, and the cumulative pore volume at pore diameters less than or equal to about 500 angstroms, measured by ASTM Test No. D 4284-03, is less than or equal to about 0.30 milliliters per gram, preferably at pore diameters less than or equal to about 400 angstroms less than about 0.30 milliliters per gram, and more preferably at pore diameters less than or equal to about 400 angstroms in the range of about 0.05 milliliters per gram to about 0.18 milliliters per gram.

The cumulative pore volume of the mordenite zeolite catalysts preferably at pore diameters less than or equal to about 300 angstroms is less than about 0.25 milliliters per gram, more preferably at pore diameters less than or equal to about 300 angstroms less than about 0.20 milliliters per gram, and most preferably at pore diameters less than or equal to about 300 angstroms in the range of about 0.08 milliliters per gram to about 0.16 milliliters per gram.

Preferably the peak macropore diameter of the above catalysts is in the range of about 400 angstroms to about 800 angstroms, more preferably the peak macropore diameter is in the range of about 400 angstroms to about 700 angstroms, and most preferably the peak macropore diameter of the catalyst is in the range of about 450 angstroms to about 600 angstroms.

The mordenite zeolite of the catalyst of the present invention has a silica to alumina molar ratio of about 50:1 to about 105:1. Preferably the mordenite zeolite has a silica to alumina molar ratio of about 65:1 to about 95:1.

The catalyst of the present embodiment may be in the form of a tablet.

A further embodiment of the present invention is directed to a catalyst composite comprising:
  (a) the mordenite zeolite catalyst of the above invention; and
  (b) a binder.

The binder in step (b) of the above process for making the mordenite zeolite catalyst composite is an inorganic material, preferably the binder is alumina.

The mordenite zeolite is present in the above catalyst composite in the range of about 50 weight percent to about 99 weight percent based on the total dry weight of the catalyst composite. Preferably the mordenite zeolite is present in the range of about 60 weight percent to about 90 weight percent based on the total dry weight of the catalyst composite.

A further embodiment of the present invention is directed to catalyst composites made by the above process.

Yet another embodiment of the present invention is directed to the process for preparing a catalyst composite comprising the steps of:
  (a) contacting a mordenite zeolite powder having a silica to alumina molar ratio in the range of about 50:1 to about 105:1 with a binder in the presence of volatiles to form a mixture wherein the weight ratio of the mordenite zeolite is range of about 50 to about 99 based on the total dry weight of the resulting catalyst composite, and wherein the volatiles in the mixture are in the range of about 30 weight percent to about 70 weight percent;
  (b) shaping the mixture to form a composite;
  (c) drying the composite; and
  (d) calcining the composite in a substantially dry environment.

In step (a) of the above process, the temperature is typically at least 15° C., preferably the temperature is at least 20° C., and more preferably the temperature is at least 27° C.

The above process further comprises addition of an shaping aid in step (a).

The shaping in step (b) in the above process preferably comprises extruding.

The drying in step (c) in the above process is typically carried out at temperatures in the range of about 100° C. to about 200° C.

Calcining in step (d) in the above process is typically carried out at temperatures in the range of about 400° C. to about 1,000° C. in a substantially dry environment.

The binder in step (a) of the above process for making the mordenite zeolite composite is an inorganic material, preferably the binder is alumina.

The volatiles in step (a) in the process for making the mordenite zeolite composite comprise water and an acid, and preferably the acid is nitric acid.

The volatiles in step (a) in the above process for making the mordenite zeolite composite further comprise a polysaccharide.

The volatiles in the mixture in step (a) in the process for making the mordenite zeolite composite are preferably in the range of about 40 weight percent to about 60 weight percent of the mixture.

In step (a) of the above process, the weight percent of the mordenite zeolite is preferably in the range of about 60 weight percent to about 90 weight percent of the mixture.

A further embodiment of the present invention is directed to catalyst composites made by the above process.

Another embodiment of the present invention is directed to a process for making an alkylated aromatic composition comprising contacting at least one aromatic hydrocarbon with at least one olefin under alkylation conditions in the presence of a catalyst having a macropore structure comprising mordenite zeolite having a silica to alumina molar ratio in the range of about 50:1 to about 105:1 and wherein the peak macropore diameter of the catalyst, measured by ASTM Test No. D 4284-03, is less than about 900 angstroms and cumulative pore volume at pore diameters less than or equal to about 500 angstroms, measured by ASTM Test No. D 4284-03, is equal to or less than about 0.30 milliliters per gram.

The above process may further comprise in step (b) the reactivation of the deactivated zeolite catalyst with a suitable solvent flush, preferably the solvent is an aromatic hydrocarbon. More preferably, the aromatic hydrocarbon is benzene.

The above process further comprises sulfonating the alkylated aromatic composition.

The aromatic hydrocarbon of the above process is benzene, toluene, xylene, cumene, or mixtures thereof. Preferably, the aromatic is benzene or toluene.

The olefin in the above process may have from about 4 carbon atoms to about 80 carbon atoms. The olefin may be an alpha olefin, an isomerized olefin, a branched-chain olefin, or mixtures thereof. The alpha olefin or the isomerized olefin may have from about 6 carbon atoms to about 40 carbon atoms, preferably from about 18 carbon atoms to about 28 carbon atoms, and more preferably from about 20 carbon atoms to about 24 carbon atoms. The branched-chain olefin may have from about 6 carbon atoms to about 70 carbon atoms, preferably from about 8 carbon atoms to about 50 carbon atoms, and more preferably from about 12 carbon atoms to about 18 carbon atoms.

The olefin of the present embodiment may be a partially-branched-chain isomerized olefin having about 6 carbon atoms to about 40 carbon atoms. Preferably, the partially-branched-chain olefin has from about 20 carbon atoms to about 40 carbon atoms.

The process of the above embodiment of the present invention for making an alkylated aromatic composition further comprises the step of isomerizing the normal alpha olefin with an isomerizing acidic catalyst before contacting the aromatic with the olefin to prepare an alkyl aromatic product where less than 40 weight percent of the alkylated aromatic hydrocarbon is 2-aryl, and at least 20 weight percent, preferably at least 75 weight percent of the alkylated aromatic hydrocarbon is a mono-alkylate.

The isomerizing acidic catalyst of the above process of the present invention for making an alkylated aromatic composition is preferably the a solid catalyst having at least one metal oxide, which has an average pore size of less than 5.5 angstroms. More preferably, that solid catalyst is a molecular sieve with a one-dimensional pore system. As used herein, the average pore size of a catalyst refers only to the pores within the active portion thereof, and does not include pores of any inactive binder or support used therewith.

The alkylation process as described above is carried out without the addition of water and using dried aromatic hydrocarbon and olefin feed. It is believed that the presence of water during the alkylation process contributes to an increase in the deactivation of the alkylation catalysts of this invention.

The alkylation processes of the above embodiments are further characterized by an increase of at least 50 hours in the alkylation run length time compared to the mordenite zeolite catalysts having a peak macropore diameter greater than 900 angstroms and a cumulative pore volume at pore diameters less than or equal to 300 angstroms greater than 0.30 milliliters per gram, preferably the increase in the alkylation run length time is at least 75 hours, and more preferably the in the alkylation run length time is at least 100 hours.

The catalysts and catalyst composites of this invention may be reactivated in situ by use of a suitable flush, such as an aromatic hydrocarbon flush, preferably the flush is with benzene.

BRIEF DESCRIPTION OF THE DRAWING

FIG. 1 is a graph showing the reactivation of Catalyst Composite 3. Preparation of Catalyst Composite 3 is described in Example 4 and its characteristics are given in Tables I and II. The data used to generate the graph in FIG. 1 is given in Table III and was collected in an alkylation reaction conducted as described in Example 7. The inlet temperature, which is the temperature of the feed entering the reactor before the reaction exotherm has developed, is also shown in the graph.

DETAILED DESCRIPTION OF THE INVENTION DEFINITIONS

The term "alkylate" means an alkylated aromatic hydrocarbon.

The term "2-aryl content" is defined as the percentage of total alkylate (the alkylate species in which the alkyl chain derived from the olefin employed in the present alkylation process is attached to the aromatic ring) that is comprised of those chemical species in which the attachment of the alkyl chain to the aromatic ring is at the 2-position along the alkyl chain.

The term "binder" means any suitable inorganic material which can serve as matrix or porous matrix to bind the zeolite particles into a more useful shape.

The term "branched-chain olefins" means olefins derived from the polymerization of olefin monomers higher than ethylene and containing a substantial number of branches wherein the branches are alkyl groups having from about one carbon atom to about 30 carbon atoms. Mixtures of ethylene and higher olefins are also contemplated.

The term "calcining" as used herein means heating the catalyst in a substantially dry environment to about 400° C. to about 1,000° C.

The term "cumulative pore volume" obtained by Mercury Intrusion Porosimetry as used herein refers to that part of the total volume in milliliters per gram derived from the graphical, cumulative pore volume distribution, measured by Section 14.1.6 of ASTM D 4284-03, or the corresponding tabular presentation of the same data between defined upper and lower pore diameters. When no lower diameter limit is defined, the lower limit is the lowest detection limit or lowest radius measured by Section 14.1.6 of ASTM D 4284-03.

The terms "dry basis", "anhydrous basis", and "volatiles-free basis" shall refer to the dry weight of catalyst composite or raw materials expressed on a metal oxides basis such as $Na_2O.Al_2O_3.xSiO_2$.

The term "flush" as used herein means contacting the deactivated catalysts and catalyst composites of this invention in the reactor with a suitable solvent, such as an aromatic hydrocarbon for reactivation of the catalysts and catalyst composites.

The term "loss-on-ignition (LOI)" as used herein means the percent weight loss of the zeolite composite or raw material samples when they are heated to 538° C. for 1 hour. When the temperature is greater than or equal to about 538° C., the "loss-on-ignition" approximates the percent volatiles.

The terms "macropore", "mesopore", and "micropore" as used herein follow the definitions set forth by the International Union of Pure and Applied Chemistry (IUPAC), Division of Physical Chemistry, in Manual of Symbols and Terminology for Physicochemical Quantities and Units, Appendix II Definitions, Terminology and Symbols in Colloid and Surface Chemistry Part 1, Adopted by the IUPAC Council at Washington, D.C., USA, on 23 Jul., 1971. Pores with widths or diameters exceeding ~50 nanometers (500 angstroms) are called "macropores". Pores with widths or diameters not exceeding ~2.0 nanometers (20 angstroms) are called "micropores". Pores of intermediate size (2.0 nanometers<width or diameter≦50 nanometers) are called "mesopores".

The term "Mercury Intrusion Porosimetry" refers to the ASTM Test No. D 4284-03 used to determine pore volume distribution of catalysts by Mercury Intrusion Porosimetry. Mercury pore distribution was measured using a Quantachrome Scanning Mercury Porosimeter Model SP-100. The software version used by the instrument is V2.11 (dated Oct. 27, 1993). Surface tension used in the calculation is 473 dynes per centimeter and the contact angle is 140 degrees.

The terms "normal alpha olefin" and "linear alpha olefin" mean those straight-chain olefins without a significant degree of alkyl branching in which the carbon to carbon double bond resides primarily at the end or "alpha" position of the carbon chain, i.e., between $C_1$ and $C_2$. Normal alpha olefins are derived from polymerization of ethylene.

The term "normal alpha olefin isomerization" means the conversion of normal alpha olefins into isomerized olefins having a lower alpha olefin content (the double bond is between $C_1$ and $C_2$), higher internal olefin content (the double bond is in positions other than between $C_1$ and $C_2$), and optionally a higher degree of branching.

The term "partially-branched chain olefin" is defined as the olefin product of isomerization of normal alpha olefins wherein the degree of branching is higher than in the starting normal alpha olefins.

The term "peak macropore diameter" as used herein means the peak diameter (i.e., the diameter within the macropore region at which the differential plot of pore size distribution, as defined by section 14.2, reaches a maximum)

in the macropore range determined by ASTM Test No. 4284-03 for the macropore peak in the catalysts of the present invention.

The term "peptizing" means the dispersion of large aggregates of binder particles, including hydrated aluminas, into much smaller primary particles by the addition of acid.

The term "percent volatiles" as used herein means the difference between the actual weight of the catalyst composite or the raw materials and the weight of the material on a substantially dry, anhydrous, or volatiles-free basis, expressed as a percentage of the actual sample weight.

The term "SAR" or "silica to alumina ratio" refers to the molar ratio of silicon oxide to aluminum oxide; mol $SiO_2$: mol $Al_2O_3$.

The term "sufficient water to shape the catalyst material" means quantity of water required to make an acid peptized mixture of zeolite and alumina powders into an extrudable mass.

The term "tabletting" as used herein refers to the process of forming a catalyst aggregate from zeolite powder or a mixture of zeolite and binder powders by compressing the powder in a die.

The term "total pore volume" obtained by Mercury Intrusion Porosimetry as used herein refers to the total pore volume in milliliters per gram derived from the graphical, cumulative pore volume distribution (Section 14.1.6 of ASTM D 4284-03) or the corresponding tabular presentation of the same data.

As used herein, all percentages are weight percent, unless otherwise specified.

As noted above, the present invention is directed to catalysts having a controlled macropore structure comprising mordenite zeolite. The catalysts of the present invention were characterized by pore volume distribution obtained by Mercury Intrusion Porosimetry, ASTM Test No. D 4284-03. Mercury Intrusion Porosimetry provides a graph of cumulative pore volume (pv) versus pore diameter (pd). Mercury Intrusion Porosimetry also is used to determine the macropore peak diameter from the derivative, delta pv ($\Delta pv$) divided by delta pd ($\Delta pd$). The graphs are used to characterize the catalysts of the present invention.

Mordenite zeolitic catalysts and catalyst composites of the present invention when used in alkylation of aromatic hydrocarbons with olefins exhibited a reduction in deactivation rates as measured by increase in alkylation run length times compared to zeolitic catalysts known in the prior art. This result was unexpected, since it had previously been believed that increasing the surface area of the catalyst would increase its activity, but was likely to also increase deactivation rates. Relative deactivation rates were determined for the catalysts of the present invention under standard alkylation reactions conditions. Results of the deactivation experiments are given in Table II. The mordenite zeolite catalyst composites of the present invention exhibit reduction in deactivation rates evidenced by substantially longer run length times compared to mordenite zeolite catalysts that do not have the macropore structure and the pore volume distribution of the mordenite zeolite catalyst composites of the present invention.

The mordenite zeolite catalysts and catalyst composites of the present invention also exhibited unexpected results in their ability to be reactivated with a flush using a suitable solvent, such as an aromatic hydrocarbon, preferably benzene. This was surprising since generally prior art zeolite alkylation catalysts cannot be easily reactivated in situ once they are deactivated. Once the prior art zeolite alkylation catalysts are completely deactivated, the reactor bed must be changed to remove the deactivated zeolite catalysts. In the case of the mordenite zeolite catalysts and catalyst composites of the present invention, all that is required is that at the end of an alkylation run the olefin feed stream is stopped while the aromatic hydrocarbon continues to be flushed through the reactor for a sufficient number of hours. Economically, the use of the mordenite zeolite catalysts and catalyst composites of the present invention for alkylation of aromatic hydrocarbons with olefins is highly desirable.

The mordenite zeolitic catalysts composites may be prepared using mordenite zeolite CBV 90A® available from Zeolyst International having a nominal silica to alumina ratio of 90:1. Any available similar mordenite zeolite may be used for preparing the mordenite zeolite catalyst composites of the present invention. It is believed that mordenite zeolite having a silica to alumina ratio between about 50:1 and about 105:1 may be used for the preparation of the mordenite catalyst composites of the present invention.

The catalysts of the present invention may be shaped or formed into tablets, extrudates or any other shape. The preparation of extrudates requires the presence of a binder, such as alumina. The tabletted catalysts do not require the presence of a binder. The crystalline mordenite zeolite powder may be compressed to form a tablet.

The alkylation reaction may be carried out by any conventionally known process. The alkylation process using the mordenite zeolite catalysts and catalyst composites of the present invention is conducted in the absence of water. The aromatic hydrocarbon is reacted with one or more olefins in the presence of a catalyst of the present invention under alkylation reaction conditions. The aromatic hydrocarbon may be single-ring or double-ring, preferably the aromatic hydrocarbon is a single-ring. The aromatic hydrocarbon may be an alkylated aromatic, such as a mono-alkylated aromatic, wherein the alkyl group has from about 4 carbon atoms to about 80 carbon atoms. When the aromatic hydrocarbon used is a mono-alkylated aromatic, the product of the alkylation reaction is a di-alkylated aromatic.

The olefins useful for alkylation of the aromatic hydrocarbons may be linear-chain or branched-chain having from about 4 carbon atoms to about 80 carbon atoms. In addition, normal alpha olefins may be isomerized to obtain partially-branched-chain olefins for use in alkylation reaction of the present invention. These resulting partially-branched-chain olefins may be alpha-olefins, beta-olefins, internal-olefins, tri-substituted olefins, and vinylidene olefins.

Procedure for Isomerization of Normal Alpha Olefins

The isomerization process may be carried out in batch or continuous mode. The process temperatures can range from 50° C. to 250° C. In the batch mode, a typical method is to use a stirred autoclave or glass flask, which may be heated to the desired reaction temperature. A continuous process is most efficiently carried out in a fixed bed process. Space rates in a fixed bed process can range from 0.1 to 10 or more weight hourly space velocity.

In a fixed bed process, the isomerization catalyst is charged to the reactor and activated or dried at a temperature of at least 150° C. under vacuum or flowing inert, dry gas. After activation, the temperature of the isomerization catalyst is adjusted to the desired reaction temperature and a flow of the olefin is introduced. The reactor effluent containing the partially-branched, isomerized olefin is collected. The resulting partially-branched, isomerized olefin contains a different olefin distribution (alpha olefin, beta olefin; internal olefin, tri-substituted olefin, and vinylidene olefin) and branching content than the unisomerized olefin.

Procedure for Alkylation of Aromatic Hydrocarbons

Alkylation of aromatic hydrocarbons with normal alpha olefins, partially-branched-chain isomerized olefins, and branched-chain olefins may be carried out by any method known by a person skilled in the art.

The alkylation reaction is typically carried out with an aromatic and an olefin in molar ratios from 1:2 to 25:1. Process temperatures can range from about 100° C. to about 250° C. As the olefins have a high boiling point, the process is preferably carried out in the liquid phase. The alkylation process may be carried out in batch or continuous mode. In the batch mode, a typical method is to use a stirred autoclave or glass flask, which may be heated to the desired reaction temperature. A continuous process is most efficiently carried out in a fixed bed process. Space rates in a fixed bed process can range from 0.01 to 10 or more weight hourly space velocity.

In a fixed bed process, the alkylation catalyst is charged to the reactor and activated or dried at a temperature of at least 150° C. under vacuum or flowing inert, dry gas. After activation, the alkylation catalyst is cooled to ambient temperature and a flow of the aromatic hydrocarbon compound is introduced, optionally toluene. Pressure is increased by means of a back pressure valve so that the pressure is above the bubble point pressure of the aromatic hydrocarbon feed composition at the desired reaction temperature. After pressurizing the system to the desired pressure, the temperature is increased to the desired reaction temperature. A flow of the olefin is then mixed with the aromatic hydrocarbon and allowed to flow over the catalyst. The reactor effluent comprising alkylated aromatic hydrocarbon, unreacted olefin and excess aromatic hydrocarbon compound is collected. The excess aromatic hydrocarbon compound is then removed by distillation, stripping, evaporation under vacuum, or any other means known to those skilled in the art.

Reactivation of Deactivated Mordenite Zeolite Catalysts and Composites

Once the mordenite zeolite catalysts and catalyst composites are completely deactivated, the alkylation reaction slows down or stops because access to the active sites is restricted by large molecular species formed by olefin polymerization that cannot diffuse out of pores containing the active sites in the zeolitic material. However, reactor bed need not be changed to remove the deactivated mordenite zeolite catalysts and catalyst composites. The deactivated mordenite zeolite catalysts and catalyst composites are reactivated at the end of an alkylation run by stopping the olefin feed stream to the reactor and permitting the aromatic hydrocarbon stream to continue to be flushed through the reactor for a sufficient time, typically from about 16 hours to about 60 hours.

EXAMPLES

Preparation of Mordenite Zeolite Alkylation Catalyst Composites

Example 1

Preparation of Comparative Catalyst Composite A

Mordenite zeolite catalyst composites were prepared by the following method:

Loss-on-ignition (LOI) was determined for a sample of a commercially available mordenite zeolite CBV 90A®, available from Zeolyst International, with a silica to alumina molar ratio of 90:1, by heating the sample to 538° C. for 1 hour. The LOI obtained was 11.56 weight % and provided the percent volatiles in the mordenite zeolite powder being used. The LOI of a commercial sample of Catapal B® hydrated aluminum oxide available from Vista Chemical Company was determined by heating the sample to 538° C. for 1 hour and was 26.01 weight %. Next, based on the results obtained from the LOI, 588 grams of mordenite zeolite powder and 175.7 grams of alumina powder were weighed out to give a total of 520 grams of mordenite zeolite powder and 130 grams of alumina powder on a volatile-free basis.

The two dry powders were manually mixed in a plastic bag and then added to a Baker Perkins mixer and dry mixed for 3 minutes. The amount of concentrated (70.7%) nitric acid to give 0.7 weight % (based on 100% nitric acid) of the dry weight of the zeolite and the alumina powders was calculated to be 12.9 grams. This amount of 70.7% nitric acid was weighed out and dissolved in 294.3 grams of deionized water.

The total amount of water and 70.7% nitric acid needed to obtain a final concentration of approximately 42% total volatiles was calculated as follows. Volatiles in the mordenite zeolite powder are 68 grams (588 gram total weight—520 grams dry weight). Volatiles in the alumina powder are 45.7 grams (175.7 grams total weight—130 grams dry weight). Nitric acid solution is considered to be 100% volatiles. Thus, if all the above raw materials were combined, the volatiles would be 420.9 grams. To give a mixture of 650 grams (520 grams zeolite and 130 grams alumina dry basis) dry powder with 42% volatiles, the total weight of the mixture must be 1120.7 grams. Thus, an additional 49.8 of deionized water must be added.

To the powders in the mixer, 50 grams of deionized water were added over a period of 17 minutes using a peristaltic pump. The mixer was then stopped so that the walls of the mixer could be scraped down. Mixing was then resumed and the solution of nitric acid in water was added over 10 minutes using the peristaltic pump. At the end of acid addition, the temperature of the wet mixture was 78° C. Mixing was continued for a total time of 40 minutes, with occasional holds to allow for scraping the sides of the mixer. At the end of the mixing period, the wet mixture consisted of large smooth clumps and the wet mixture temperature was 42° C. At this point, the volatiles were 41.45 weight %.

The wet mixture was extruded through 1.27 millimeter, asymmetric quadrilobe die inserts, in a Ram extruder. The wet long cylindrical strands were dried at 121° C. for 8 hours. The long cylindrical strands were then broken to give extrudates with length to diameter ratio of 2:3. The extrudates were sieved and the portion larger than 1.7 millimeters was retained.

The extrudates were then calcined in a substantially dry environment in a muffle furnace using the following temperature program:

The extrudates are heated to 593° C. over two hours, then held at 593° C. for 1.8 hours and next cooled to 204° C. A total of 1681 grams of extrudates were obtained.

Mercury Intrusion Porosimetry showed the extrudates to have a peak macropore diameter of 1000 angstroms and a cumulative pore volume at diameters less than 300 angstroms of 0.1587 ml/gram.

Example 2

Preparation of Catalyst Composite 1

Mordenite zeolite catalyst composite was prepared following the procedure used in Example 1 above, with the following exceptions:

Volatiles of the mordenite zeolite powder and alumina powder were 11.63 weight % and 27.54 weight %, respectively. Corresponding mordenite zeolite and alumina powders were 1176.9 grams and 358.8 grams, respectively. Concentrated nitric acid, 25.8 grams, was dissolved in 600 grams deionized water. The powders were dry mixed for 10 minutes and 80.3 grams of water was added over 15 minutes. The acid solution was added over 10 minutes at which point the temperature of the mixture was 23° C. The steam/water mixer was adjusted to give a jacket temperature of 48° C. Mixing was continued for 30 minutes. At this point, the mixture was too pasty, so mixing was continued for 20 minutes with the mixer cover off. Volatiles were 40.41 weight % at extrusion time. The mixture was then extruded, dried, sized and calcined in a substantially dry environment.

Mercury Intrusion Porosimetry showed the peak macropore diameter to be 574 angstroms and the cumulative pore volume at diameters less than 300 angstroms to be 0.1661 ml/gram.

Example 3

Preparation of Catalyst Composite 2

This catalyst composite was made by the procedure described in Examples 1 and 2 above with the following exceptions:

Volatiles of the zeolite powder and alumina powder were 11.63 weight % and 27.54 weight %, respectively. Corresponding amounts of zeolite and alumina powders were 1176.9 grams and 358.8 grams, respectively. The acid solution was made from 25.8 grams of 70.7% nitric acid and 600 grams of deionized water. Added water was 80.3 grams. After 10 minutes of dry mixing the powders, water was added over 15 minutes. Next, the acid solution was added over 10 minutes, which point the temperature of the mixture was 48° C. Mixing was continued for 30 minutes. At this time, the mixture was too pasty, so mixing was continued for 20 minutes with the mixer cover off. Volatiles were 40.41 weight % at extrusion time. After extruding, drying, sizing, and calcining in a substantially dry environment, Mercury Intrusion Porosimetry showed the peak macropore diameter to be 768 angstroms and the cumulative pore volume at diameters less than 300 angstroms to be 0.1617 ml/gram.

Example 4

Preparation of Catalyst Composite 3

Mordenite zeolite catalyst composite was prepared following the procedure used in Example 1 above, with the following exceptions:

Volatiles of the mordenite zeolite powder and alumina powder were 10.79 weight % and 25.72 weight %, respectively. Corresponding mordenite zeolite and alumina powders were 582.91 grams and 175.03 grams, respectively. Concentrated nitric acid, 12.9 grams, was dissolved in 300 grams deionized water. The powders were dry mixed for 10 minutes and 179.12 grams of water was added over 11 minutes. The acid solution was added over 9 minutes. At this point, the mixture had a thick liquid consistency and the temperature of the mixture was 23° C. Heat was applied to the mixer to raise the temperature to 46° C. A stream of air was injected into the mixing chamber to dry the mixture. After mixing for 40 minutes under these conditions, the volatiles were 42.55% and the mixture looked rubbery. Mixing was continued for 10 minutes without added heat or air. At this point, the mixture looked rubbery and wet. Mixing was continued for 25 minutes with a stream of air at which time the mixture was still rubbery and the temperature of the mixture was 41° C. Volatiles were 41.34 weight %. Mixing was continued for an additional 20 minutes with application of heat. The temperature of the mixture was 47° C. and the volatiles were 39.93% at this time. The wet mixture had a clay like consistency. The mixture was then extruded through a 1/16 of an inch, asymmetric quadrilobe die inserts, in a Ram extruder, dried, sized and calcined in a substantially dry environment.

Mercury Intrusion Porosimetry showed the peak macropore diameter to be 645 angstroms and the cumulative pore volume at diameters less than 300 angstroms to be 0.1617 ml/gram.

Example 5

Preparation of Catalyst Composite 4

Mordenite zeolite catalyst composite was prepared following the procedure used in Example 1 above, with the following exceptions:

Volatiles of the mordenite zeolite powder and alumina powder were 12.04 weight % and 26.98 weight %, respectively. Corresponding mordenite zeolite and alumina powders were 1182.2 grams and 356.1 grams, respectively. Concentrated nitric acid, 25.8 grams, was dissolved in 600 grams deionized water. The powders were dry mixed in a plastic bag for 2 minutes and then dry mixed in the Baker-Perkins mixer for 10 minutes before 288.7 grams of water was added over 15 minutes. The acid solution was added over 10 minutes. At this point, the mixture had a consistency of a thick liquid and the temperature of the mixture was 21° C. Heat was applied to the mixer to raise the jacket temperature to 46° C. A stream of air was injected into the mixing chamber to dry the mixture. After mixing for 40 minutes under these conditions, the volatiles were 44.73% and the temperature was 36° C. Mixing was continued for 10 minutes at which point the temperature of the mixture was 39° C. and the mixture looked rubbery. After an additional mixing for 25 minutes, the mixture formed large clumps and mixed well. Mixing was continued for an additional 2 minutes without a stream of air. At this point, the temperature of the mixture was 41° C. and the volatiles were 38.99% at this time. The wet mixture had a clay-like consistency. The mixture was then extruded through a 1.27 millimeters, asymmetric quadrilobe die inserts, in a Ram extruder, dried, sized and calcined in a substantially dry environment.

Mercury Intrusion Porosimetry showed the peak macropore diameter to be 570 angstroms and the cumulative pore volume at diameters less than 300 angstroms to be 0.1711 ml/gram.

The Mercury Intrusion Porosimetry results for the mordenite zeolite catalyst composites of Examples 1–5 are given below in Table I.

TABLE I

| Catalyst Composite | Mercury Intrusion Porosimetry Properties | | |
|---|---|---|---|
| | Total PV* (ml/gram) | PV <300 angstroms** (ml/gram) | Macropore peak diameter (angstroms) |
| Comparative A*** | 0.462 | 0.1587 | 1000 |
| 1 | 0.344 | 0.1661 | 574 |
| 2 | 0.346 | 0.1617 | 768 |
| 3 | 0.329 | 0.1617 | 645 |
| 4 | 0.318 | 0.1711 | 570 |

*Total pore volume.
**Total pore volume at diameters less than or equal to 300 angstroms.
***Catalyst Composite A was used as a comparative catalyst composite for obtaining deactivation rates of Catalysts Composites 3 and 4. The temperature during binding and mixing of the mordenite zeolite and the binder was not adjusted between 45° C. and 50° C. for the preparation of the Comparative Catalyst Composite A. The temperature during binding and mixing of the mordenite zeolite and the binder was adjusted between 45° C. and 50° C. for the preparation of the Catalyst Composites 1–4.

Example 6

Preparation of Isomerized Normal Alpha Olefins

Typically, isomerization of normal alpha olefins is carried out as described below:

$C_{20}$–$C_{24}$ normal alpha olefin with the following composition was used for this Example:

Alpha olefin 89.1%
Beta olefin 0.5%
Internal olefin 1.4%
Tri-substituted olefin 0.2%
Vinylidene olefin 9.5% (determined by carbon nuclear magnetic resonance spectroscopy)
Branched-chain olefin 11% (determined by infra red spectroscopy)

The normal alpha olefin was pumped up-flow through a fixed-bed reactor (570 millimeters high and with an inside diameter of 22.3 millimeters) containing 65 grams of solid olefin isomerization. The reactor was operated isothermally at 160° C. at a liquid to hourly space velocity of 0.5 per hour and at atmospheric pressure.

The reactor effluent containing the partially branched, isomerized olefin is collected. The resulting partially-branched, isomerized olefin contains a different olefin distribution (alpha-olefin, beta-olefin; internal-olefin, tri-substituted-olefin and vinylidene-olefin) and branching content than the un-isomerized olefin.

Example 7

Preparation of Alkylbenzene Compositions

Typically, alkylation of aromatic hydrocarbons with normal alpha olefins, partially-branched-chain isomerized olefins and branched-chain olefins was carried out as described below:

A fixed bed reactor was constructed from 15.54 millimeters Schedule 160 stainless steel pipe. Pressure in the reactor was maintained by an appropriate back pressure valve. The reactor and heaters were constructed so that adiabatic temperature control could be maintained during the course of alkylation runs. A bed of 170 grams of 850 micrometer to 2 millimeters Alundum particles was packed in the bottom of the reactor to provide a pre-heat zone. Next, 100 grams of Catalyst Composite 3 was charged to the fixed bed reactor. Finally, void spaces in the catalyst bed were filled with 309 grams of 150 micrometers Alundum particles interstitial packing. The reactor was gently vibrated while charging catalyst and alundum to ensure a high packed bulk density. After charging, the reactor was closed, sealed, and the pressure was tested.

The alkylation catalyst was then heated to 200° C. under a 20 liters per hour flow of nitrogen measured at ambient temperature and pressure and dehydrated for 23 hours at 200° C. The catalyst bed was then cooled to 100° C. under nitrogen. Benzene was then introduced into the catalytic bed in an up-flow manner at a flow rate of 200 grams per hour. Temperature (under adiabatic temperature control) was increased to a start-of-run inlet temperature of 154° C. (measured just before the catalyst bed) and the pressure was increased to 12.66 atmospheres.

When temperature and pressure had lined out at desired start-of-run conditions of 154° C. and 12.66 atmospheres, a feed mixture, consisting of benzene and $C_{20-24}$ NAO at a molar ratio of 15:1 and dried over activated alumina, was introduced in an up-flow manner at 200 grams per hour. As the feed reached the catalyst in the reactor, reaction began to occur and internal catalyst bed temperatures increased above the inlet temperature. After about 8 hours on-stream, reactor exotherm was 20° C. In the first 57 hours on-stream, the olefin conversion decreased from 100% to 98.8% (Run Period 1). At this point, the catalyst bed was flushed with benzene at 200 grams per hour during 18 hours. Following the benzene flush, the benzene and olefin feed flow was resumed. Inlet temperature was increased to 162° C. at 57 run hours. Feed was continued until 351 run hours (Run Period 2 from 57 to 351 run hours). Olefin conversion was initially 98.9% during Run Period 2 but declined to 98.1% at 321 run hours and further to 95.3% at 351 run hours. A second benzene flush was performed at 351 run hours during 17 hours. After the second benzene flush, feed flow was resumed again to start Run Period 3. Feed was continued until 550 run hours. Olefin conversion was initially 98.5% but declined to 98.3% at 519 run hours and to 97.0% at 550 run hours. A third benzene flush was done during a weekend. Feed flow was resumed after the third benzene flush to begin Run Period 4. At the beginning of Run Period 4, olefin conversion was 98.8% and at 942 run hours the olefin conversion was 98.4%. The run was stopped after 942 hours on-stream but could have continued longer.

Alkylated aromatic hydrocarbon products containing excess benzene were collected during the course of the run. After distillation to remove excess aromatic hydrocarbon, analysis showed that greater than 97% conversion of olefin was achieved during most of the course of the run.

Example 8

Procedure for Measuring Deactivation Rates of the Catalysts in Alkylation Reactions Deactivation rates of the mordenite zeolite alkylation catalysts were measured during the alkylation reaction similar to the alkylation reaction in Example 7 above.

The alkylation reaction was carried out as described above. As the alkylation reaction was exothermic, a temperature exotherm was measured by means of appropriately located thermocouples in the catalyst bed. Using temperature profile data from a catalyst run, the position of the temperature exotherm in the bed was plotted as a function of time, in hours. The deactivation rate of the catalyst is the slope of this line in centimeters per hour. Relative deactivation rates are determined from the relative alkylation run lengths. All catalysts were evaluated at standard conditions of temperature, pressure, and space velocity and the alkylation run lengths were measured in hours.

Comparative Catalyst Composite A was prepared as described above in Example 1 and shown in Table I.

The deactivation test was conducted during alkylation of benzene with an isomerized $C_{20}$ to $C_{24}$, low alpha content olefin at a temperature of 170° C. The molar ratio of benzene to olefin was in the range of 10:1 to 15:1.

Alkylation run lengths of Catalyst Composites 3 and 4 prepared as described in Examples 4 and 5 and in Table I are shown relative to the alkylation run length of Comparative Catalyst Composite A and are given in Table II below.

TABLE III

| Experiment | Catalyst Composite | Run Number | Inlet Temperature (° C.) | Alkylation Run Time (hours) | Benzene Flush After Run (hours) |
|---|---|---|---|---|---|
| 1 | 3 | 1 | 154 | 57* | 18 |
| 1 | 3 | 2 | 162 | 294 | 17 |
| 1 | 3 | 3 | 170 | 198 | Weekend end**** |
| 1 | 3 | 4 | 172 | 363 | 16 |
| 1 | 3 | 5 | 172 | 30** | — |
| 2 | 3 | 1 | 154 | 184 | 25 |

TABLE II

| | | | | Mercury Intrusion Porosimetry | | | Alkylation |
|---|---|---|---|---|---|---|---|
| Catalyst Composite | Temperature (° C.) | Silica: Alumina Molar Ratio | Zeolite (%) | Total PV* (ml/gram) | PV < 300 Å (ml/gram) | Peak Macropore Diameter, Å | Run Length (hours) |
| 3 | 162 | 90 | 80 | 0.329 | 0.166 | 645 | 293 |
| 4 | 166 | 90 | 80 | 0.318 | 0.162 | 570 | 200 |
| A | 170 | 90 | 80 | 0.361 | 0.159 | 1000 | 30 |

Example 9

Procedure for the Reactivation of Deactivated Catalysts in Alkylation Reactions

Catalyst Composite 3 prepared in Example 4 was used for conducting the reactivation experiments. Comparative Catalyst Composite A prepared in Example 1 was used for comparison in the reactivation experiments. Characteristics obtained by Mercury Intrusion Porosimetry for all three catalysts are shown above in Table II.

The alkylation reactions for reactivation of the deactivated alkylation catalysts and catalyst composites of this invention were conducted as described above in Example 7.

The inlet temperature was recorded at the start of the alkylation reaction. The inlet temperature is the temperature of the feed entering the reactor before the reaction exotherm has developed. Deactivation of Catalyst Composite 3 and Comparative Catalyst Composite A was observed when the position of the exotherm moved away from the inlet zone, of the reactor. Once the Catalyst Composites were completely deactivated, the alkylation reaction was stopped by stopping the flow of the olefin feed to the reactor and the reactor was flushed with benzene by continuing the flow of the benzene feed for about 16 hours to about 60.

At the end of the benzene flush, the alkylation reaction was again started by beginning the flow of the olefin feed and the alkylation reaction was allowed to proceed until the position of the exotherm again moved away from the inlet zone of the reactor. Two reactivation experiments were run with Catalyst Composite 3, which was reactivated four and two times, respectively, with a benzene flush. Comparative Catalyst A was flushed once with benzene for 43 hours, a much longer period than in the case of Catalyst Composite 3, without being reactivated.

Table III below and FIG. 1 show the reactivation data collected during the alkylation reactions conducted as in Example 9.

TABLE III-continued

| Experiment | Catalyst Composite | Run Number | Inlet Temperature (° C.) | Alkylation Run Time (hours) | Benzene Flush After Run (hours) |
|---|---|---|---|---|---|
| 2 | 3 | 2 | 174 | 96*** | 43 |
| 2 | 3 | 3 | 190 | 217 | — |
| 3 | Comparative A | 1 | 176 | 44 | 43 |
| 3 | Comparative A | 2 | 159 | 24 | — |

*The concentration of the unreacted olefin was observed to increase rapidly which was presumed to indicate deactivation of Catalyst Composite 3. A benzene flush was conducted to reactivate Catalyst Composite 3.
**The experiment was conducted to determine whether a shorter period of benzene flush, 16 hours, would be sufficient to reactivate Catalyst Composite 3. The alkylation run was stopped after 30 hours, but it is believed that the alkylation run could have been allowed to run for a longer period of time.
***Comparative Catalyst A was observed to deactivate very rapidly. A benzene flush of 43 hours did not reactivate Comparative Catalyst A.
****The benzene flush was started on Friday evening by stopping the flow of the olefin feed to the reactor and allowed to continue until the following Monday morning, at which time the flow of the olefin feed was again started.

What is claimed is:

1. A catalyst having a macropore structure comprising mordenite zeolite having a silica to alumina molar ratio in the range of about 50:1 to about 105:1 and wherein the peak macropore diameter of the catalyst, measured by ASTM Test No. D 4284-03, is less than about 900 angstroms and the cumulative pore volume of the catalyst at pore diameters less than or equal to about 500 angstroms, measured by ASTM Test No. D 4284-03, is less than or equal to about 0.30 milliliters per gram.

2. The catalyst of claim 1 wherein the cumulative pore volume at pore diameters less than or equal to about 400 angstroms is less than or equal to about 0.30 milliliters per gram.

3. The catalyst of claim 2 wherein the cumulative pore volume at pore diameters less than or equal to about 300 angstroms is less than or equal to about 0.25 milliliters per gram.

4. The catalyst of claim 3 wherein the cumulative pore volume at pore diameters less than or equal to about 300 angstroms is less than or equal to about 0.20 milliliters per gram.

5. The catalyst of claim 4 wherein the cumulative pore volume of the catalyst at pore diameters less than or equal to about 400 angstroms is in the range of about 0.05 milliliters per gram to about 0.18 milliliters per gram.

6. The catalyst of claim 5 wherein the cumulative pore volume of the catalyst at pore diameters less than or equal to about 300 angstroms is in the range of about 0.08 milliliters per gram to about 0.16 milliliters per gram.

7. The catalyst of claim 1 wherein the peak macropore diameter is in the range of about 400 angstroms to about 800 angstroms.

8. The catalyst of claim 7 wherein the peak macropore diameter is in the range of about 400 angstroms to about 700 angstroms.

9. The catalyst of claim 8 wherein the peak macropore diameter of the catalyst is in the range of about 450 angstroms to about 600 angstroms.

10. The catalyst of claim 1 wherein the mordenite zeolite has a silica to alumina molar ratio of about 65:1 to about 95:1.

11. The catalyst of claim 10 wherein the mordenite zeolite has a silica to alumina molar ratio of about 75:1 to about 90:1.

12. The catalyst of claim 1 wherein the catalyst is in the form of a tablet.

13. A catalyst composite comprising:
    (a) the catalyst of claim 1; and
    (b) a binder.

14. The catalyst composite of claim 13 wherein the binder is alumina.

15. The catalyst composite of claim 13 wherein the mordenite zeolite is present in the range of about 50 weight percent to about 99 weight percent based on the total dry weight of the catalyst composite.

16. The catalyst composite of claim 15 wherein the mordenite zeolite is present in the range of about 60 weight percent to about 90 weight percent based on the total dry weight of the catalyst composite.

17. A process for preparing a catalyst composite wherein the peak macropore diameter of the catalyst, measured by ASTM Test No. D 4284-03, is less than about 900 angstroms and the cumulative pore volume of the catalyst at pore diameters less than or equal to about 500 angstroms, measured by ASTM Test No. D 4284-03, is less than or equal to about 0.30 milliliters per gram, comprising:

(a) contacting a mordenite zeolite having a silica to alumina molar ratio in the range of about 50:1 to about 105:1 with a binder in the presence of volatiles to form a mixture wherein the weight percent of mordenite zeolite is in the range of about 50 to about 99 based on the total dry weight of the resulting catalyst composite, and wherein the volatiles in the mixture are in the range of about 30 weight percent to about 70 weight percent of the mixture;
   (b) shaping the mixture to form a composite;
   (c) drying the composite; and
   (d) calcining the composite in a substantially dry environment.

18. The process of claim 17 wherein in step (b) shaping comprises extruding.

19. The process of claim 17 wherein in step (a) the weight percent of mordenite zeolite is in the range of about 60 to about 90 based on the total weight of the mixture.

20. The process of claim 17 wherein the binder is alumina.

21. The process of claim 17 wherein in step (a) the volatiles in the mixture are present in the range of about 35 weight percent to about 50 weight percent of the mixture.

22. The process of claim 21 wherein the volatiles comprise water and an acid.

23. A catalyst composite prepared by the process of claim 17.

* * * * *